United States Patent
Brown et al.

(10) Patent No.: US 10,181,317 B2
(45) Date of Patent: *Jan. 15, 2019

(54) HIGH-FREQUENCY ULTRASOUND IMAGING SYSTEM

(75) Inventors: Jeremy Brown, Halifax (CA); Robert Bruce Alexander Adamson, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 1936 days.

This patent is subject to a terminal disclaimer.

(21) Appl. No.: 13/146,620

(22) PCT Filed: Feb. 26, 2010

(86) PCT No.: PCT/IB2010/000813
§ 371 (c)(1),
(2), (4) Date: Oct. 7, 2011

(87) PCT Pub. No.: WO2010/097710
PCT Pub. Date: Sep. 2, 2010

(65) Prior Publication Data
US 2012/0016243 A1    Jan. 19, 2012

Related U.S. Application Data

(60) Provisional application No. 61/156,049, filed on Feb. 27, 2009.

(51) Int. Cl.
*G10K 11/36* (2006.01)
*G10K 11/34* (2006.01)
(Continued)

(52) U.S. Cl.
CPC .............. *G10K 11/346* (2013.01); *A61B 1/00* (2013.01); *G10K 11/36* (2013.01); *H03H 9/0296* (2013.01)

(58) Field of Classification Search
CPC ..... G10K 11/356; G10K 11/36; H03H 9/0296
(Continued)

(56) References Cited

U.S. PATENT DOCUMENTS 3,675,163 A * 7/1972 Hartmann et al. ............ 333/150
3,696,312 A * 10/1972 Kuhn et al. ................. 333/24 R
(Continued)

FOREIGN PATENT DOCUMENTS

EP    0098579 A2    1/1984

OTHER PUBLICATIONS

Alpinion Medical Systems, NPL, "Research on PMN-PT Single Crystal," pp. 1-4, for details of lead-magnesium-niobate lead-titanate, which was first made in 1997 (see p. 2, paragraph 2).*
(Continued)

*Primary Examiner* — Jennifer Dieterle
*Assistant Examiner* — Vani Gupta
(74) *Attorney, Agent, or Firm* — Quarles & Brady LLP

(57) ABSTRACT

A high frequency ultrasound analog beamformer comprises a linear array of surface acoustic wave (SAW) devices formed on a single crystal piezoelectric substrate, such as a PMN-PT single crystal piezoelectric substrate. Each SAW device comprises ultrasound input and output electrode structures separated by a variable delay structure. The beamformer further comprises a delay controller operably connected to each variable delay structure to control the delay of each SAW device to dynamically focus signals received at each input electrode.

37 Claims, 11 Drawing Sheets

(51) Int. Cl.
*H03H 9/02* (2006.01)
*A61B 1/00* (2006.01)

(58) Field of Classification Search
USPC .............................. 600/407, 437, 459, 462
See application file for complete search history.

(56) References Cited

U.S. PATENT DOCUMENTS

| | | | |
|---|---|---|---|
| 3,845,420 A * | 10/1974 | Holland | H03H 9/423 |
| | | | 310/313 B |
| 3,893,047 A * | 7/1975 | Lardat | 333/153 |
| 3,952,269 A * | 4/1976 | Bristol | H03H 9/02771 |
| | | | 29/25.35 |
| 4,117,424 A * | 9/1978 | Coldren | H03H 9/02716 |
| | | | 333/142 |
| 4,244,037 A * | 1/1981 | Jelks | 367/121 |
| 4,245,333 A * | 1/1981 | Jelks | G10K 11/346 |
| | | | 333/150 |
| 5,345,426 A | 9/1994 | Lipschutz | |
| 5,469,851 A | 11/1995 | Lipschutz | |
| 5,522,391 A * | 6/1996 | Beaudin et al. | 600/443 |
| 5,784,336 A * | 7/1998 | Gopinathan et al. | 367/123 |
| 6,425,869 B1 * | 7/2002 | Rafter et al. | 600/458 |
| 6,500,120 B1 * | 12/2002 | Anthony | G01S 7/5208 |
| | | | 600/437 |
| 6,705,995 B1 | 3/2004 | Poland et al. | |
| 7,569,971 B2 * | 8/2009 | Andle et al. | 310/313 D |
| 2003/0171655 A1 * | 9/2003 | Newman et al. | 600/200 |
| 2004/0064044 A1 | 4/2004 | Brock-Fisher | |
| 2007/0230759 A1 * | 10/2007 | Tamura | 382/128 |
| 2007/0232906 A1 * | 10/2007 | Alexandru | G01N 29/262 |
| | | | 600/437 |

OTHER PUBLICATIONS

Uchino et al. (NPL, "Introduction to Piezoelectric Actuators and Transducers"); Pennsylvania State University publication; pp. 17-18.*
PCT International Search Report and Written Opinion, PCT/IB2010/000813, dated Aug. 9, 2010, 8 Pages.

* cited by examiner

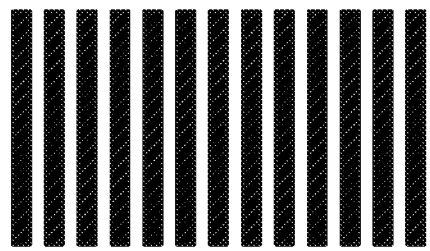
FIG. 1A – Prior Art
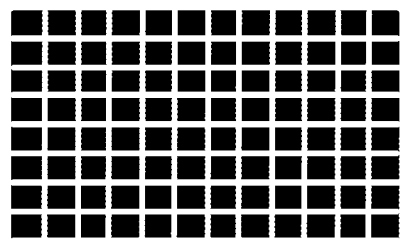
FIG. 1B – Prior Art
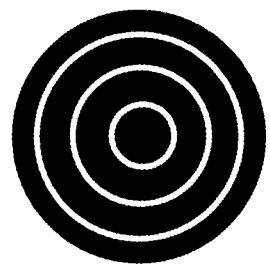
FIG. 1C – Prior Art

HIGH-FREQUENCY ULTRASOUND IMAGING SYSTEM

FIELD OF TECHNOLOGY

The present disclosure relates to a high-frequency ultrasound imaging system.

BACKGROUND

Low-frequency (<20 MHz) ultrasound is one of the most common imaging modalities in diagnostic medicine. The success of this modality can mostly be attributed to its ability to provide safe, reliable, real-time images of sub-surface tissue structures. Over the last 50 years, technological advancements in low-frequency ultrasound hardware and fabrication equipment have enabled an increasing level of sophistication in these systems.

In contrast, high-frequency ultrasound is a relatively new area of ultrasonic imaging that provides an order of magnitude improvement in image resolution compared with conventional low-frequency systems. Although these high-frequency systems can resolve tissue structures smaller than 50 microns in size, they are not routinely used in clinical practice. One of the barriers preventing their adoption and clinical utility is that the current systems are based on single-element geometrically-shaped transducers that have conventionally produced images with a limited depth-of-field, limited penetration depth, and relatively slow frame-rate.

In low-frequency ultrasound systems, drastic improvements in both frame-rate and depth-of-field have been achieved by replacing the single-element transducer with a transducer array and an electronic beamformer. The combination of a transducer array and an electronic beamformer allows the ultrasound energy to be electronically focused at a wide range of depths within the tissue at increased framerates. Consequently, there has been a great deal of interest in developing array-based systems for ultrasound frequencies greater than 20 MHz.

Unfortunately, fabricating high-frequency transducer arrays and associated beamformers is complicated by the increased ultrasound frequency. In particular, to produce a tightly collimated ultrasound beam, array elements with extremely small dimensions are needed and the digital sampling resolution of the electronic beamformer has to be greatly increased. Although some success in developing high-frequency transducer arrays has been recently reported, the intended applications for these arrays are somewhat limited. The transducer arrays are designed for use in general topical applications in which relatively large apertures and packaging are of no concern.

Improvements in high-frequency ultrasound imaging systems are therefore desirable.

SUMMARY

Embodiments of the invention include a high-frequency ultrasound analog beamformer based on surface acoustic wave (SAW) delays. In one embodiment, an analog beamformer comprises a linear array of SAW devices formed on a single crystal piezoelectric substrate, such as a PMN-PT single crystal piezoelectric substrate. Each SAW device comprises ultrasound input and output electrode structures separated by a variable delay structure. The input and output electrode structures can be interdigital electrode structures. The beamformer further comprises a delay controller operably connected to each variable delay structure to control the delay of each SAW device to dynamically focus signals received at each input electrode prior to output. According to some embodiments, the variable delay structure can be formed of planar electrodes formed on opposite surfaces of the substrate, and the controller can comprise means to apply a voltage across the variable delay structure to control the length of the variable delay structure. An adder adds the output signals of each SAW device. In one embodiment, this addition can be provided by forming the output electrode structures of a plurality of SAW devices as a single electrode structure to sum the variably delayed signals received from the plurality of input electrode structures.

Other aspects of the invention include systems and applications for the devices described above, and methods corresponding to all of the foregoing. For example, the beamformer can be used in a high frequency ultrasound imaging system, or a high frequency endoscopic ultrasound probe having a form factor and packaging suitable for in-vivo imaging of inner ear structures through the round window membrane.

BRIEF DESCRIPTION OF THE DRAWINGS

Embodiments of the present disclosure will now be described, by way of example only, with reference to the attached Figures.

FIG. 1A is a schematic representation of conventional transducer array having a linear array geometry.

FIG. 1B is a schematic representation of conventional transducer array having a two-dimensional array geometry.

FIG. 1C is a schematic representation of conventional transducer array having an annular array geometry.

The figures depict embodiment of the invention for purposes of illustration only. One skilled in the art will readily recognize from the following discussion that alternative embodiments of the structures and methods illustrated herein may be employed without departing from the principles of the invention described herein.

DETAILED DESCRIPTION

Prior to a detailed description of embodiments of a high-frequency ultrasound imaging beamformer and system, a brief description of various aspects of an ultrasound imaging system is provided.

Transducer Arrays

The structure of an array transducer is similar to that of single element transducers in many ways. For example, array transducers are composed of a piezoelectric sandwiched between a lossy backing layer and a matching layer(s). The piezoelectric resonator in an array transducer, however, is diced to produce a series of individual array elements. FIGS. 1A, 1B, and 1C illustrate the front faces of three common array geometries. The array shown in FIG. 1A is a linear array, the array shown in FIG. 1B is a two-dimensional (2-D) array, and the array shown in FIG. 1C is an annular array.

Linear array transducers, such as the example shown in FIG. 1A, have the ability to focus the ultrasound energy at any depth in the tissue, along a line parallel to the row of array elements. The ability to focus ultrasound energy at any depth in the tissue makes linear array transducers more attractive than single element transducers because the depth of field is greatly increased. The ultrasound beam is passively focused in the elevation direction (perpendicular to the row of elements) using an acoustic lens or geometric curving. There are two types of linear arrays: one referred to as a "linear array" and the other referred to as a "phased array."

Figure 2:
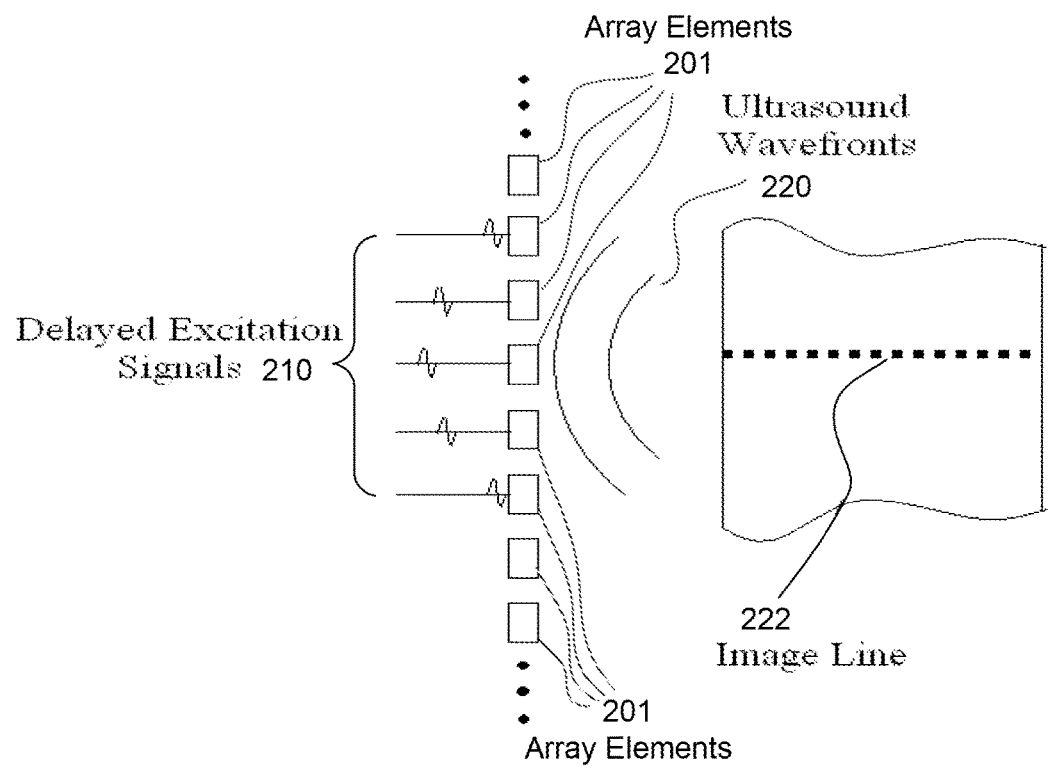
FIG. 2 is a schematic representation of beamforming using a linear array.

"Linear arrays" focus the ultrasound beam perpendicular to the array using a sub-aperture of array elements. FIG. 2 illustrates a group of array elements 201 used to form an active aperture. The group of array elements are excited using a pattern of delayed excitation signals 210 to produce ultrasound wavefronts 220 that are focused along an image line 222 perpendicular to the array. Additional image lines are obtained by shifting the active aperture across the array. A sub-aperture of elements steps across a much larger aperture, collecting the parallel A-scans needed to produce a 2-D image. A typical linear array will have a total aperture consisting of 256 elements, and use a sub-aperture of 64 elements with wavelength spacing $\lambda$ between the array elements 201.

Figure 3:
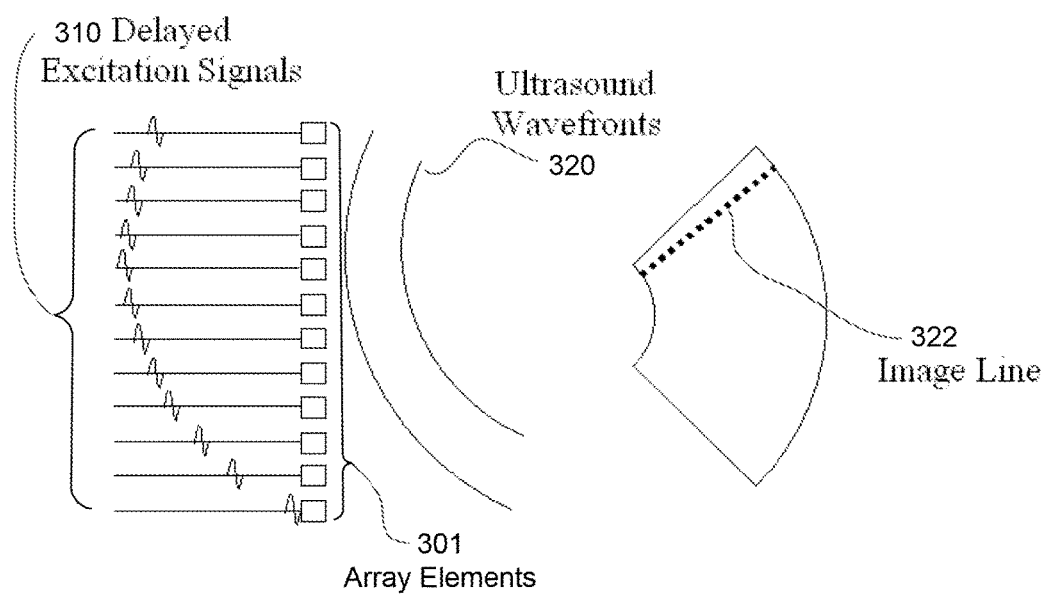
FIG. 3 is a schematic representation of beamforming using a phased array.

FIG. 3 illustrates the second version of a linear array, the "phased array," that has the ability to steer the ultrasound wavefronts 320. The elements 301 in the phased array are excited using a pattern of delayed excitation signals 310 that focuses and steers the ultrasound wavefronts 320. Consequently, the image line 322 is no longer perpendicular to the array. Additional image lines are obtained by changing the steering angle. By steering the ultrasound beam at different angles, a series of A-scans are collected. These A-scans are used to generate a sector format image. As a result, phased arrays can have a large field of view with a relatively small aperture. Typically, a phased array will use 128 elements with half-wavelength spacing between the array elements 301. Generally, other than the smaller element spacing and aperture size, phased arrays are similar to linear arrays.

Although annular arrays, such as the example shown in FIG. 1C, are a suitable for many topical applications in high-frequency imaging, due to their relatively large element sizes and low element counts, they do not have the ability to beam steer or translate the aperture electronically and therefore need to be mechanically scanned. This means that the fixed aperture needs to be relocated in space in order to generate the parallel "lines of sight" that make up a 2D image. This creates a larger "effective" aperture limiting the packaging size, image scan window, and frame-rate. High-frequency linear array transducers can potentially overcome many of the problems inherent to annular arrays. For example, linear arrays that are 3 mm or less in total aperture can be manufactured. Linear array transducers can be fabricated on high-frequency piezo-composite materials and use geometric elevation focusing to avoid the need for an acoustic lens.

Transmit Beamforming

It is convenient to separate an ultrasound beamformer into two parts: the transmit beamformer, which generates the sequence of high voltage pulses required to excite the array and focus the transmitted energy; and the receive beamformer, which focuses the received signals. The operation of the transmit beamformer will be described with reference to FIG. 4.

Figure 4:
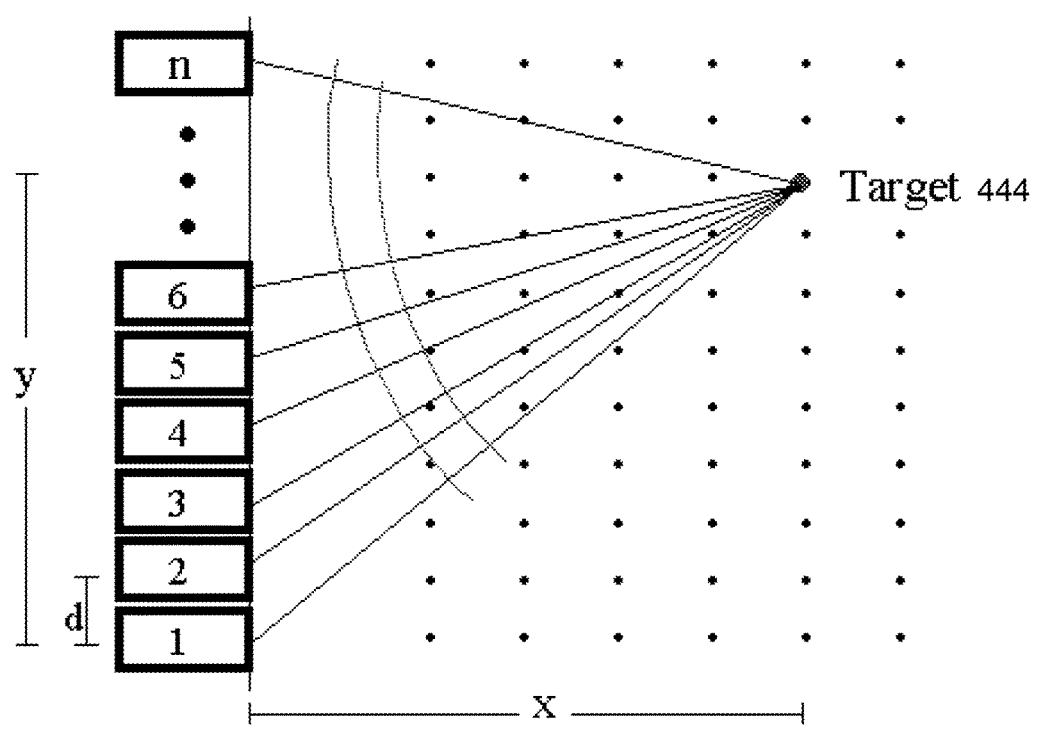
FIG. 4 is a schematic representation of a geometrical arrangement of an array and a desired focal point within an imaging medium.

FIG. 4 illustrates a geometrical arrangement of an array of elements 1 through n (in cross-section) that are each separated by distance d, and a desired focal point, target 444, within an imaging medium. The lines connecting the transducer array elements 1 through n to the target 444 show the paths from each element to the target 444. In order to focus the transducer radiation to a target 444, the path length distances from each of the transducer elements 1 through n to the target 444 must be determined. Then the delay pattern to apply to signals to the transducer elements 1 through n that is required to focus the sound waves to the target 444 can be determined.

The path length from each of the transducer elements 1 through n to the target is calculated based on geometric analysis.

$$l_n(x,y) = \sqrt{(y-d_n)^2 + x^2} \tag{1}$$

In equation (1), $l_n$ is the distance from the nth transducer element to the desired (x,y) coordinate. If a constant speed of sound within the medium is assumed, the total time it takes a pulse to travel from the nth transducer element to the target is $l_n/c_o$, wherein $c_o$ is the assumed speed of sound within the medium.

In order to create constructive interference at the desired focal distance, a delay pattern is inserted so that all the pulses from transducer elements 1 through n arrive at the target 444 at the same time. These delays are calculated by subtracting the maximum element to target flight time given by equation 2.

$$\Delta\tau_n(x, y) = \frac{\sqrt{(y-d_n)^2 + x^2}}{c_o} - \frac{\sqrt{y^2 + x^2}}{c_o} \qquad \text{Eqn. (2)}$$

In equation (2), $\Delta\tau_n$ corresponds to the excitation delay for element n. Because a transmit beamformer can only focus at one depth for each transmit event, the transmitted wave is allowed to disperse before subsequent transmit pulses are applied.

Receive Beamforming

Figure 5:
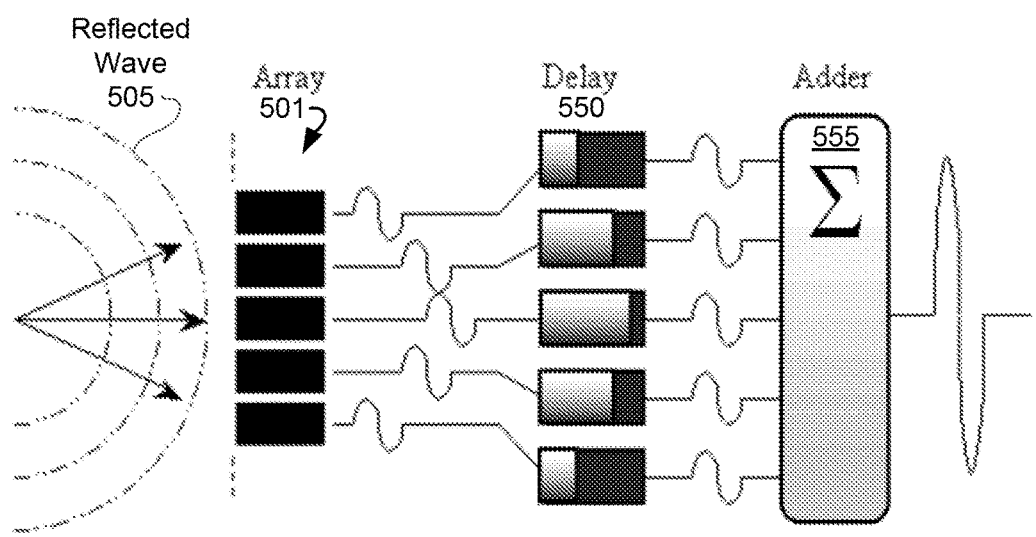
FIG. 5 is a schematic representation of receive beamforming.

Analogous to the transmit beamforming; the radiation pattern that is received by the array can also be focused. The echo from a small object in the body will arrive back at different array elements at slightly different times. By delaying the signals from different elements to account for the difference in arrival times, the echoes can be re-aligned so that they will add coherently. A flow diagram of receive beamforming is shown schematically in FIG. 5. The transducers (array elements 501) receive the reflected wave 505 and the signals produced are delayed in a phased pattern using delay devices 550 to create constructive interference upon summation at adder 555.

The receive beamforming process is similar to transmit focusing with a difference: in transmit focusing, pulses can only be focused to one depth in the tissue at a time, whereas in receive beamforming it is possible to dynamically change the delay pattern applied to the echoes as they are received. In a sense, receive beamforming allows one to approximate the radiation pattern of a geometrically shaped transducer whose geometric focus is sweeping forward at the speed of sound. Like transmit beamforming, the delay pattern for the transducer elements in the array 501 is related to the time of flight between the element and the target.

Overview of High-Frequency Ultrasound Imaging

High frequency ultrasound has the ability of provide much higher image resolution than conventional (low frequency) ultrasound systems, albeit while achieving lower penetration depth. Although high-frequency ultrasound has been implemented in some clinical applications such as intravascular imaging, ophthalmic imaging and pre-clinical applications, it has not been widely accepted as a diagnostic tool since these systems are based on single-element mechanically translated transducers with a limited depth-of field. As a result, attempts are being made to develop high-frequency linear arrays. Previously, optical coherence tomography (OCT) has been used as a high-resolution imaging tool for the ex-vivo inner ear. Although these results are encouraging, OCT imaging unfortunately cannot penetrate into tissues more than a couple of millimeters. There has been some previous work on developing high-frequency linear array beamformers that are capable of generating real-time images, including development of an analog beamformer based on tapped delay lines.

Separately, variable surface acoustic wave (SAW) delay lines have also been developed. Previous work shows that by placing an electric field across a SAW device, the delay time between the two electrodes can be significantly and accurately changed. These results have shown that the delay time on a lithium niobate substrate can be dynamically changed beyond +/− 5 ns. In a digital beamformer, the focusing delays are usually inserted after the signals from the elements have been digitized. This makes developing high-frequency digital beamformer for linear array transducers very challenging and expensive due to the extremely high sampling resolution required and large element count.

High-Frequency Analog Beamformer

As an alternative to a digital beamformer, a high frequency analog beamformer based on SAW delays is provided in accordance with an embodiment of the invention. An advantage of the analog beamformer is that all of the channels are summed into one before the signal is digitized. This drastically reduces the cost and complexity of the beamformer.

Figure 6:
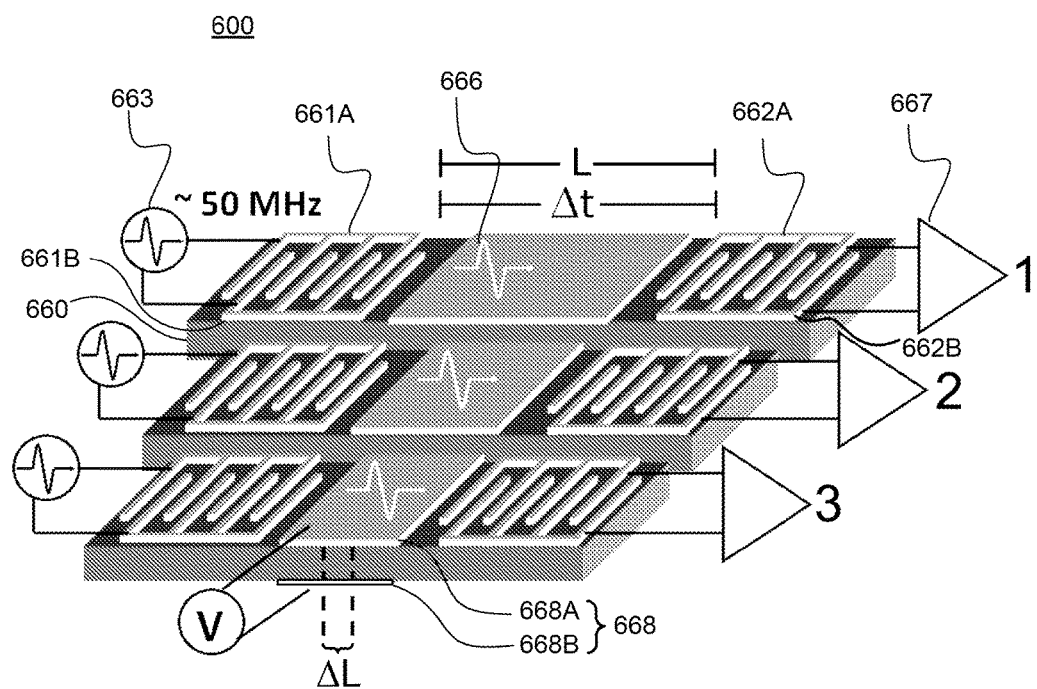
FIG. 6 is a schematic diagram of a three-channel surface acoustic wave beamformer in accordance with an exemplary embodiment.

An example of a three channel SAW beamformer 600 is shown in FIG. 6. Similar to imaging transducers, SAW devices are also based on piezoelectric substrates 660. For each channel 1, 2, 3 of the SAW beamformer 600, the SAW device comprises two sets of electrodes in the form of interdigitated fingers 661A, 661B and 662A, 662B, one set at each end of a bulk piezoelectric substrate 660. When an electronic signal 663 is used to excite one set of electrodes (input electrode structure) 661A, 661B, an ultrasonic wave 666 is generated within approximately 1 micron of the surface of the substrate 660. It will then take a certain amount of travel time Δt for the surface wave 666 to travel the length of the substrate 660 between the sets of electrodes 661A, 661B and 662A, 662B and arrive at the second set of electrodes (output electrode structure) 662A, 662B. When the surface wave 666 arrives at the second set of electrodes 662A, 662B, an electrical signal 667 proportional to the input signal 663 is produced. The travel time Δt of the acoustic wave 666 between the electrode sets 661A, 661B and 662A, 662B corresponds to the electrical delay of the SAW device for the corresponding channel 1, 2, or 3.

In an exemplary embodiment, as shown in FIG. 6, the SAW device has a second set of plate electrodes 668A, 668B on the top and bottom of the substrate 660 forming a variable delay structure 668 between the two sets of SAW electrodes 661A, 661B and 662A, 662B for each channel 1, 2, 3. By applying a voltage V across these plate electrodes 668A, 668B, the length of the piezoelectric substrate 660 of the SAW device expands or contracts in proportion to the 3-1 coefficient of the piezoelectric and direction of the field. By changing the physical distance L between the input electrodes 661A, 661B and output electrodes 662A, 662B, by an amount ΔL, the delay time Δt is also changed. If the delay time Δt is rapidly and accurately controlled for the individual array elements in an analog beamformer, the beamforming delays can be inserted before the signals are digitized.

The rapid and accurate control of the delay time for the individual array elements provides a significant advantage to the analog beamformer in that the delayed signals 667 from the elements can be added together before digitization and therefore, only one channel needs to be digitized. Reducing the number of digitized channels to one drastically reduces the cost of the beamformer. If the transducer array elements are connected to the SAW array elements, a simple delay control system can be used to dynamically beamform the ultrasound energy. The delay control system can apply slowly varying high-voltage electric fields to the individual plate electrodes 668A, 668B in the center of the SAW delay line. The varying high-voltage electric fields will then control the physical dimensions of the piezoelectric delay lines and hence the beamforming delay values. Since the change in the length of the substrate 660 with electric field is proportional to the length/thickness ratio, fabricating long thin SAW devices can produce the largest delay range and/or lowest control voltage. In addition, the delay range (strain) may also be maximized by choosing piezoelectrics with a large $d_{31}$ coefficient, such as PMN-PT single crystals.

Referring again to FIG. 6, there is shown a three channel SAW beamformer 600, according to an embodiment. The SAW beamformer has three different delays because a different voltage V is applied to the plate electrodes 668A, 668B corresponding to each of the channels 1, 2, 3, resulting in three different lengths L of the bulk substrate 600. Fabrication of these devices involves accurate lapping of the substrate, high-resolution photolithography of the inter-digital electrodes, and an interconnect based on ultrasonic wire bonding. Preferably, the inter-digital electrode pattern would be in the 'double electrode' transducer format in order to avoid the 'triple-transit' effect, in which waves reflecting off the receive electrode propagate back to the transmit electrode, and reflect back to the receive electrode, resulting in a spurious echo.

Another advantage of the analog beamformer based on SAW delay lines is that the signal filtering can be done with the SAW devices. SAW filters are commonly known devices to those of skill in the art, and the bandwidth of the filter is dependent on the number of interdigital electrodes in the transmit and receive surface electrodes. Therefore the signal filtering can also be accomplished in the analog domain as part of the actual piezoelectric beamformer.

Figure 7:
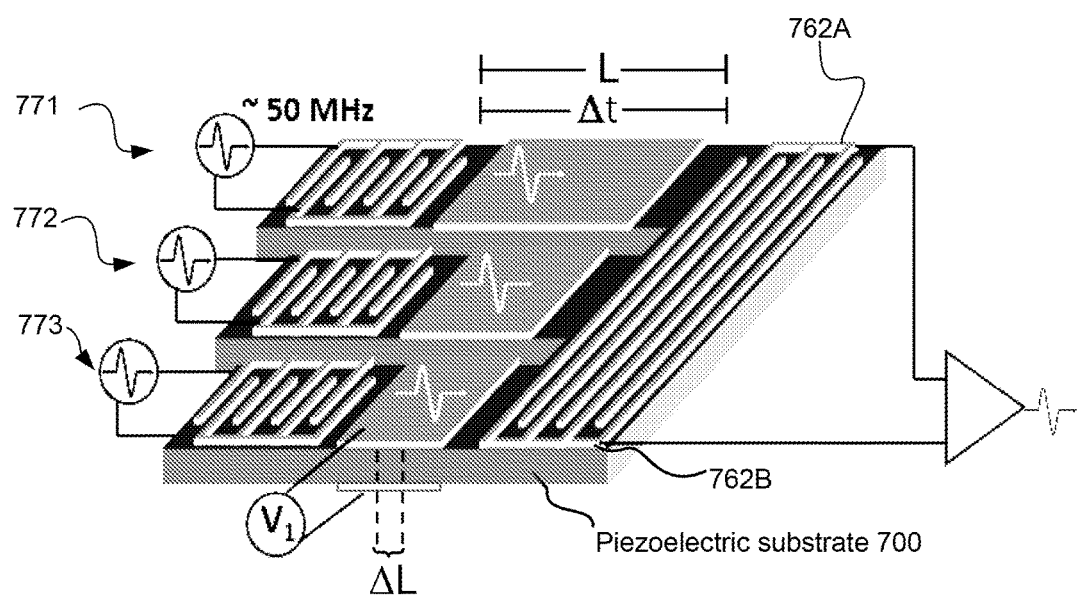
FIG. 7 is a schematic diagram of a three-channel surface acoustic wave beamformer in accordance with another exemplary embodiment.

Additionally or alternatively, in another embodiment of the analog beamformer, the signals can be added together within the piezoelectric device by expanding an interdigital electrode across all of the variable SAW delay lines that share a common strip of bulk piezoelectric substrate. FIG. 7 illustrates the alternate arrangement in accordance with another embodiment of the analog beamformer. In this example, the output electrodes 762A, 762B receive the signals from all three SAW delay lines 771, 772, 773 that share a piezoelectric substrate 700. Adding the signals together can be accomplished passively in this arrangement and no summing amplifier is required. This again reduces the cost and complexity of the beamformer, especially when there is a large element count.

In another embodiment, an analog receive-beamformer based on SAW delays described above is used to dynamically focus the ultrasound energy generated by the array transducers. Dynamic receive beamformers work by focusing the ultrasound energy after receiving the ultrasound echoes from different points in space. To focus on a single point in space, the receive delays for the individual elements are adjusted so that the difference in arrival times from the focal point to the array elements are aligned (and constructively interfere when added together). As mentioned above, to dynamically focus the array upon receiving the echoes, the focal point is swept-forward at the speed of sound as the transmit pulse travels through the tissue (or a target of interest). In an embodiment, the analog receive beamformer uses a lead magnesium niobate-lead titanate (PMN-PT) single crystal as the SAW substrate. The large $d_{31}$ coefficient inherent to these next generation piezoelectrics can significantly increase the delay range.

In another embodiment, the variable delay structures of the beamformer are formed from a photoconductive layer on the surface of a SAW device. In a piezoelectric medium, a surface wave velocity is different depending on whether the surface is conductive or insulating. For an insulating surface, charge accumulates on the surface and moves along with the wave, so that areas of negative surface displacement have negative charge and areas of positive surface displacement have positive charge. These charges attract and repel each other which effectively increases the stiffness of the material and hence increases the speed of sound. When a conductive layer is placed on the surface the charges become free to move along the surface in such a way as to cancel each other and there is no longer a surface charge contribution to the stiffness. If a thin photoconductive layer such as ZnO or CdSe, for example, is placed on the surface, then the surface conductivity and hence the speed of sound can be controlled by adjusting the amount of light striking the surface. When light hits the surface, free carriers are generated and the surface conductivity increases.

In one embodiment, the photoconductive layer is thin enough to have a negligible effect on the surface wave. In one implementation, the layer is thin compared to the wavelength of the surface acoustic wave at the operating frequency, for example a wavelength of approximately 20 to 40 μm. A surface layer less than one tenth of the wavelength of the surface wave (e.g. less than 2-4 μm) can be expected to have a negligible effect on the wave propagation. This is a reasonable thickness suitable for deposition by sputtering. In one embodiment, the thickness is essentially independent of the photoconductive material used. Thinner photoconductive layers will be less photoconductive, but this can be compensated for by increasing illumination, doping, or various other techniques.

Figure 8A:
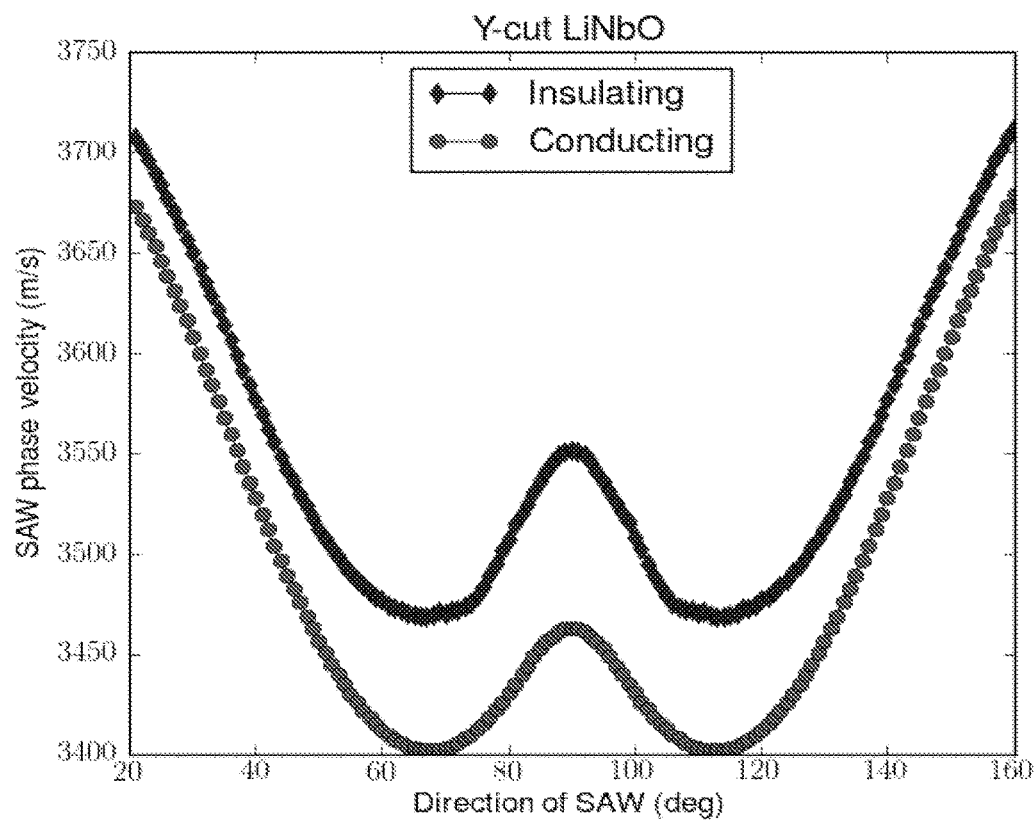
FIG. 8A illustrates calculated SAW velocities in y-cut lithium niobate for insulating and conducting surfaces.
Figure 8B:
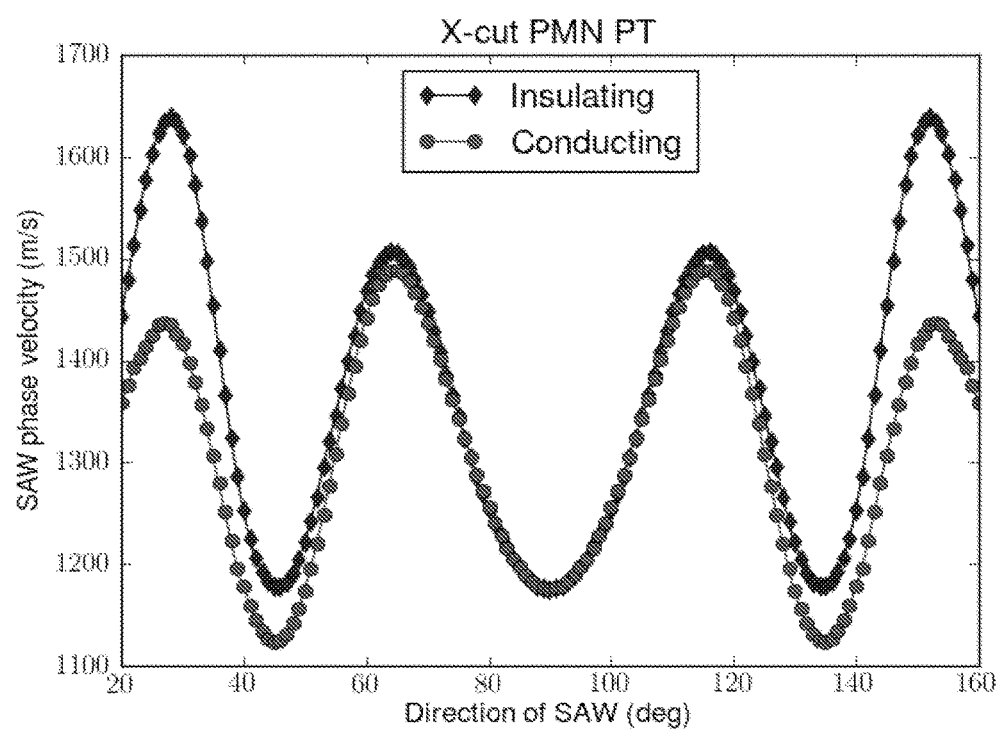
FIG. 8B illustrates calculated SAW velocities in x-cut lead magnesium niobate-lead titanate for insulating and conducting surfaces.

Our models show that the effect of light hitting the surface of a photoconductive layer can result in a very significant change in the speed of a surface wave. FIG. 8A illustrates calculated SAW velocities in y-cut lithium niobate for insulating and conducting surfaces. The maximum fractional difference between conducting and insulating surface velocities is 3.4% at 90 degrees. FIG. 8B illustrates calculated SAW velocities in x-cut lead magnesium niobate-lead titanate for insulating and conducting surfaces. The maximum fractional difference between conducting and insulating surface wave velocities is 18% at 25 degrees relative to the [001] crystal axis. Thus, whereas relying only on the piezoelectric stretching of the SAW layer may achieve approximately a 1% change in delay, the use of a conductive layer can cause a much larger effect. Accordingly, the device can be made much smaller, which would be a considerable manufacturing advantage. The delay will scale with the SAW velocity. Thus, an implementation that achieves an 18% change in SAW velocity could result in a device that is 18 times shorter than the length of a device that only changes the delay by 1% by relying on piezoelectric stretching. For example, a 30-40 mm long device with a 1% strain can be replaced by a device having the same control that is only 2 mm long using the change in SAW velocity. Accordingly, the task of incorporating large numbers of SAW delays into a single package, for example hundreds of SAW delays for a linear array beamformer, can be simplified.

High-Frequency Ultrasound Imaging System Including an Analog Beamformer

Figure 9:
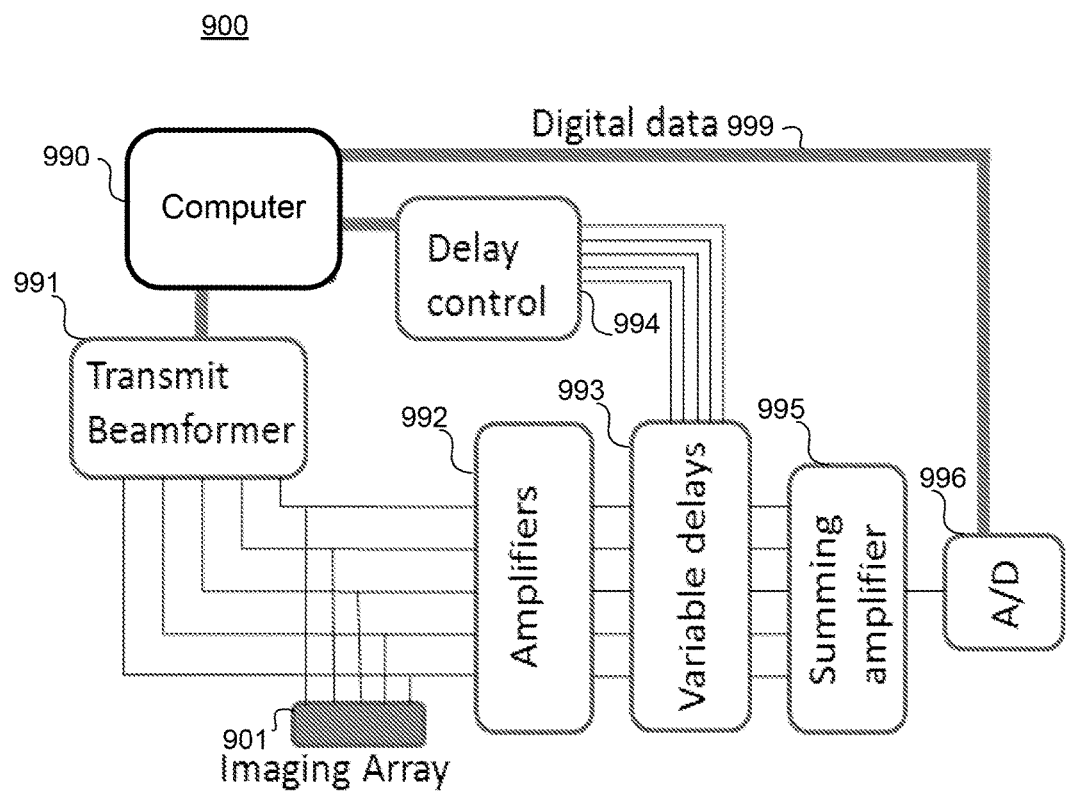
FIG. 9 illustrates a block diagram of a high-frequency ultrasound imaging system utilizing an analog surface acoustic wave beamformer in accordance with an embodiment.

FIG. 9 shows a block diagram of a high-frequency ultrasound imaging system 900 utilizing an analog SAW beamformer in accordance with an embodiment. The computer 990 controls a transmit beamformer 991 with a fixed number of transmit focal zones. The transmitted pulses reflect off of tissue structures (or target areas) and are received by the elements in the imaging array 901. These signals received at the imaging array 901 are directed through amplifiers 992 that are connected between the elements of the imaging array 901 and the individual variable delay channels 993. The computer 990 also controls the delay of each individual channel via a delay control circuit 994. The delay control circuit 994 controls the delay of each channel with a high-voltage analog signal. After the received signals are delayed appropriately by the variable delay channels 993 so as to accomplish dynamic receive beamforming, the signals are added together. This can be done either actively through an analog-summing amplifier 995 or passively by the SAW beamformer itself, for example, as described above and illustrated in FIG. 7. A single beamformed channel is then digitized by an analog to digital converter 996, and the digital data 999 is transferred back to the computer 990 for image processing.

Sufficient variation in delay can be obtained with these systems 900 using suitable substrates in order to focus a high-frequency linear array. For a 40 MHz linear array with a sub-aperture of approximately 2 mm focusing the beam between f-1.5 and f-4.5, the maximum delay range required is based on the difference in arrival time for pulse echoes between the closest and farthest elements at the lowest f-number focal point. This corresponds to a required delay range of approximately 90 ns. While previous studies have shown that delay ranges 10 ns and greater are possible with lithium niobate as the SAW device substrate, the delay range can be greatly increased by using PMN-PT single crystal as the substrate.

Laser Doppler measurements on 30 mm-long, 150-μm thick PMN-PT substrates have been performed and average lateral strains of 16 microns for plate voltages of 80V have been obtained. This is as expected for PMN-PT as it has a $d_{31}$ constant greater than −1000. Therefore, if the variation in delay were assumed to be solely proportional to the change in separation distance between the two electrodes, a voltage of +/−300 V would be required. Although this is a relatively high voltage, it is very low in current/power consumption. In addition, modeling has suggested that a much lower voltage would be required in order to accomplish this beamforming. This is because the delay variation is actually proportional to the change in separation distance as well as the change in speed of sound for the propagating surface wave.

Further embodiments of the high-frequency ultrasound imaging system can include SAW correlation and convolution filters. Correlation filters use a variable electrode spacing or apodization to implement a filter with a specific impulse response. If the impulse response is the time-reverse of the excitation pulse used, then the electrical output of the filter is the cross-correlation between the impulse response and the signal. This can be used to implement coded-excitation ultrasound with, for example, a chirped impulse response and signal. SAW convolutions use piezoelectric non-linearity to produce an electrical output signal that is the convolution of two electrical input signals. Arbitrarily programmable analog filters can thus be made by changing one of the input signals. Moreover, this allows to optimally detect signals in noise and to adaptively optimize the filter impulse response to maximize detection.

In other embodiments, a bulk wave piezoelectric delay line rather than a surface wave device can be used. Bulk wave delay lines propagate compressional bulk waves instead of surface waves. An advantage of a bulk wave device is that because it uses multiple reflections off of the outer walls of the piezoelectric to accomplish a large delay in a relatively small package, a relatively large delay variation can be accomplished by adding the plate electrodes to the top and bottom surface with a relatively small voltage (i.e. same percentage in shifting the total delay time equals a large total variation in delay). Another advantage of a bulk wave beamformer is that it could be incorporated into the same piezoelectric substrate as the imaging transducer.

Applications

As an exemplary embodiment of the application of the high-frequency ultrasound imaging system, a high-resolution ultrasound endoscope packaged for in-vivo imaging sub-surface structures of the ear and auditory system is now described. As described earlier, the system comprises an analog beamformer, based on next-generation piezoelectric substrates, that avoids the need for 1) a large number of digital channels and 2) exceedingly high sampling rates. Such a beamformer has the potential to drastically reduce the cost of any high-frequency array-based ultrasound system, and greatly increase clinical adoption of this technology.

According to the National Institute on Deafness and Other Communication Disorders, hearing loss affects approximately 10% of the general population and 40% of those over 65. There are two main forms of hearing loss, conductive loss, which is typically due to a mechanical problem with the ossicular chain of the middle ear and sensorineural loss, which is due to a failure of the transduction of sound into neural impulses in the cochlea or 'inner ear'. Both kinds of hearing loss are commonly treated by surgical interventions ranging from insertion of ossicular prostheses to cochlear implants. Many of these interventions require precise placement of implants, but very few imaging techniques are available to surgeons undertaking these delicate operations. Moreover, the etiology of hearing disorders can be very difficult owing to the overlap of symptoms between differing pathologies. In particular, while inner ear hearing loss is extremely common, there is no current imaging modality that allows visualization of the microscopic anatomy of the inner ear in-vivo, resulting in very crude etiologic diagnostics.

The high-frequency ultrasound imaging system described herein can improve diagnostics, interventions, and therapeutic monitoring of ear disorders. The high-frequency ultrasound imaging system described herein can be specifically designed and adapted for imaging structures of the ear and auditory system. This new diagnostic imaging approach can improve the objectivity and quality of diagnosis in this field of medicine, allowing physicians to apply more precisely targeted interventions.

Figure 10:
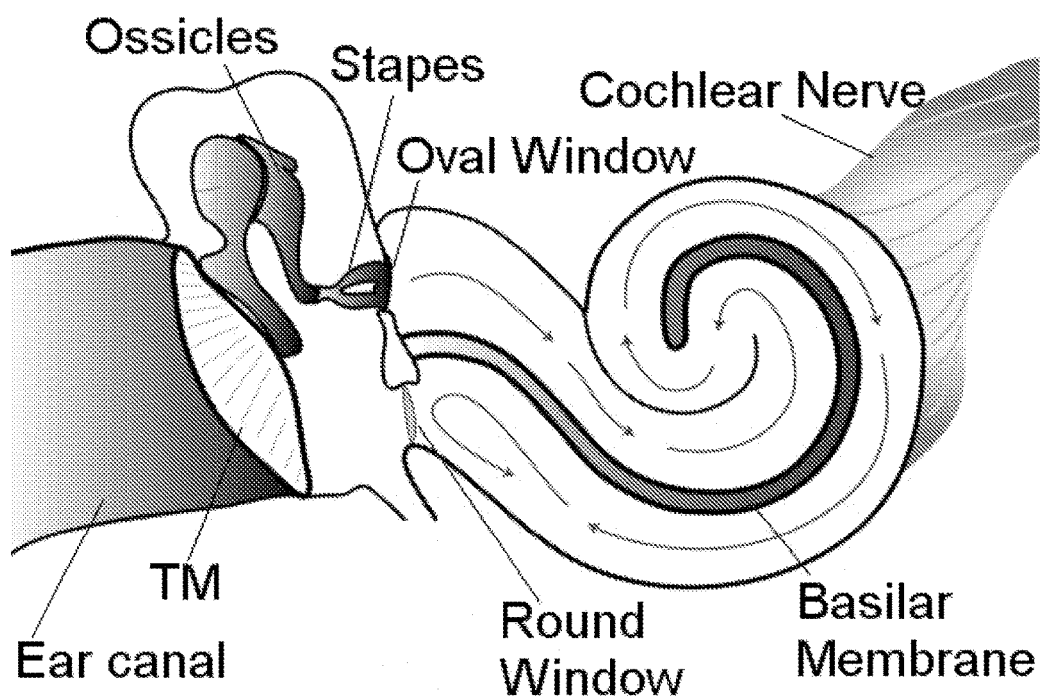
FIG. 10 is an illustration of the major components of the human ear.

FIG. 10 shows some of the larger clinically relevant structures of the auditory system. Sound is received through the external ear canal and vibrations are picked up via the tympanic membrane and passed through the ossicular chain in the middle ear. The middle ear ossicles form a chain of three bones (malleus, incus, and stapes) connecting the tympanic membrane (TM) to the cochlea. The stapes footplate sends vibrations into the cochlear fluid through the oval window at the basal end of the cochlea. As pressure is applied at the oval window by the stapes, pressure release is provided for the incompressible fluid at the round window membrane (RWM). The pressure difference across the basilar membrane creates a travelling wave that travels from the basal to the apical ends of the cochlea. Hair cells distributed along the basilar membrane oscillate in response to the fluid motion, and deflection of their stereociliae causes the opening of ion channels that release neurotransmitter and stimulate auditory nerve cells.

Common imaging methods currently used in otology are otoscopy (optical microscopy), magnetic resonance imaging (MRI), and computed tomography (CT). While otoscopy is a simple and effective means of observing the external ear canal and the tympanic membrane, it provides a poor method for observing structures of the middle and inner ear because the TM is a semi-opaque structure that scatters light. Other in-vivo imaging techniques, such as MRI and CT, do not have the spatial resolution to properly visualize the micro-anatomy of the middle and inner ear. In addition, neither of these techniques have the ability to observe the acousto-mechanical vibrations of inner ear structures in response to acoustic stimuli due to the low temporal resolution inherent to these modalities.

Other than the round and oval windows, the cochlea is completely surrounded by dense bone. There are some channels directed intracranially, such as the vestibular and cochlear aqueducts, but these are not accessible. Therefore, the most logical approach to image the cochlea with an ultrasonic endoscope is through the RWM. A RWM imaging probe designed similarly to a conventional catheter-based probe used in intravascular ultrasound imaging, but three to four times larger (due to the larger diameter of the access route), can be used for imaging the cochlea. To access the cochlea in-vivo, the imaging probe has to pass through the middle ear through a small hole in the eardrum created for this purpose. This can be created during a routine and minor clinic procedure (myringotomy). The middle ear ossicles could also potentially be imaged with ultrasound in an even less invasive manner by placing an endoscopic probe through the ear canal against the tympanic membrane. Such a probe, which could be up to 5 mm in diameter, would image across the tympanic membrane into the middle ear. In an in-vivo situation, the middle ear would need to be filled with a liquid such as water or saline in order to provide the necessary acoustic coupling required for ultrasound imaging. This can be relatively easily accomplished in the clinic with a transtympanic needle, such as those routinely used for injection of drugs such as Gentamicin or steroids.

The high-frequency ultrasound imaging system in accordance with an embodiment comprises an endoscopic probe, an analog receive beamformer, and associated image manipulation elements. The system can be used for in-vivo animal imaging and human trials. The system will first be characterized by imaging fresh cadaveric ear structures and the clinical value will be carefully assessed. Other applications include implementing a pulsed-wave Doppler component to the system in order to investigate the acousto-mechanical vibrations of the clinically relevant structures within the auditory system as an acoustic stimulus (sound) is applied.

The above described embodiment of the high-frequency ultrasound imaging system has enormous potential as a diagnostic tool in otology. In the middle ear, direct visualization of scar tissue and state of the ossicles would greatly enhance diagnosis of conductive hearing disorders and also provide a non-surgical means of assessing the performance of middle ear implants, commonly used to reconstruct the ossicular chain. For imaging the cochlea, visualizing in-vivo, for the first time, the basilar membrane, the round window membrane, and stria vascularis, diagnostics of inner ear disorders such as Meniere's disease, sudden and subacute sensorineural hearing loss, autoimmune inner ear disease, and perilymphatic fistula could be revolutionized. Various embodiments described above also have applications as an intraoperative guidance tool during cochlear implantation surgery (to visualize the placement of electrodes) and during acoustic neuroma surgery (to visualize remaining tumor and distinguish it from brainstem).

While the exemplary embodiment has been described as applied to the in-vivo imaging of the ear and auditory system, embodiments of the high-frequency ultra sound imaging system can also be applied to ophthalmic imaging, intravascular imaging, small animal imaging, dermal imaging and any other application where short range high-resolution ultrasound imaging can be used.

Other Configuration Considerations

In the description above, for purposes of explanation, numerous details are set forth in order to provide a thorough understanding of the present invention. However, it will be apparent to one skilled in the art that these specific details are not required in order to practice the present invention. In other instances, well-known electrical structures and circuits are shown in block diagram form in order not to obscure the present invention. For example, specific details are not provided as to whether the embodiments of the invention described herein are implemented as a software routine, hardware circuit, firmware, or a combination thereof.

Embodiments of the invention may be represented as a software product stored in a machine-readable medium (also referred to as a computer-readable medium, a processor-readable medium, or a computer usable medium having a computer readable program code embodied therein). The machine-readable medium may be any suitable tangible medium, including magnetic, optical, or electrical storage medium including a diskette, compact disk read only memory (CD-ROM), memory device (volatile or non-volatile), or similar non-transitory storage mechanism. The machine-readable medium may contain various sets of instructions, code sequences, configuration information, or other data, which, when executed, cause a processor to perform steps in a method according to an embodiment of the invention. Those of ordinary skill in the art will appreciate that other instructions and operations necessary to implement the described invention may also be stored on the machine-readable medium. Software running from the machine-readable medium may interface with circuitry to perform the described tasks.

While the embodiments described herein are directed to particular implementations of the high-frequency ultrasound imaging system and the method for controlling the high-frequency ultrasound imaging system, upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the devices, systems, and methods herein without departing from the spirit and scope of the invention defined in the appended claims.

What is claimed is:

1. A high frequency ultrasound analog beamformer, comprising:
   a linear array of surface acoustic wave (SAW) devices formed on a single crystal piezoelectric substrate, each SAW device of the linear array comprising ultrasound input and output electrode structures separated by a respective variable delay structure; and
   a delay control circuit operably connected to each variable delay structure to control, in the acoustic analog domain, a delay of each SAW device to dynamically focus signals received at each input electrode.

2. The beamformer of claim 1, wherein each respective variable delay structure is formed of a set of two planar electrodes comprising one planar electrode on each of two opposite surfaces of the substrate.

3. The beamformer of claim 2, wherein the delay control circuit applies a voltage across each respective set of planar electrodes to control the length of each respective variable delay structure.

4. The beamformer of claim 1, wherein each respective variable delay structure is formed of a photoconductive layer on a surface of the respective SAW device.

5. The beamformer of claim 1, further comprising an adder to add the output signals of each SAW device of the linear array.

6. The beamformer of claim 1, wherein the ultrasound output electrode structure of all SAW devices in the linear array is formed as a single electrode pair to sum the variably delayed signals received from the input electrode structures of all SAW devices in the linear array.

7. The beamformer of claim 1, wherein the input and output electrode structures are interdigital electrode structures.

8. The beamformer of claim 1, wherein the single crystal piezoelectric substrate is a PMN-PT single crystal piezoelectric substrate.

9. A high-frequency ultrasound imaging system comprising:
   an imaging array;
   a high-frequency ultrasound transmit beamformer to focus signals transmitted by the imaging array to a target;
   a high-frequency ultrasound analog receive beamformer to focus signals received by the imaging array, the beamformer comprising:
   a linear array of surface acoustic wave (SAW) devices formed on a single crystal piezoelectric substrate, each SAW device of the linear array comprising ultrasound input and output electrode structures separated by a respective variable delay structure; and
   a delay control circuit operably connected to each variable delay structure to control, in the acoustic analog domain, a delay of each SAW device to dynamically focus signals received at each input electrode; and
   processing circuitry to image the focused signals.

10. A high frequency endoscopic ultrasound probe comprising:
   an imaging array;
   a high-frequency ultrasound transmit beamformer to focus signals transmitted by the imaging array to a target;
   a high-frequency ultrasound analog receive beamformer to focus signals received by the imaging array from the target, the beamformer comprising:
   a linear array of surface acoustic wave (SAW) devices formed on a single crystal piezoelectric substrate, each SAW device of the linear array comprising ultrasound input and output electrode structures separated by a respective variable delay structure; and
   a delay control circuit operably connected to each variable delay structure to control, in the acoustic analog domain, a delay of each SAW device to dynamically focus signals received at each input electrode; and
   processing circuitry to image the focused signals.

11. The probe of claim 10 having a size suitable for in-vivo imaging of inner ear structures.

12. The probe of claim 11, wherein the size of the probe is suitable for imaging inner ear structures through a round window membrane of an inner ear.

13. The beamformer of claim 2, wherein the input and output electrode structures are interdigital electrode structures.

14. The beamformer of claim 3, wherein the input and output electrode structures are interdigital electrode structures.

15. The beamformer of claim 4, wherein the input and output electrode structures are interdigital electrode structures.

16. The beamformer of claim 5, wherein the input and output electrode structures are interdigital electrode structures.

17. The beamformer of claim 6, wherein the input and output electrode structures are interdigital electrode structures.

18. The beamformer of claim 2, wherein the single crystal piezoelectric substrate is a PMN-PT single crystal piezoelectric substrate.

19. The beamformer of claim 3, wherein the single crystal piezoelectric substrate is a PMN-PT single crystal piezoelectric substrate.

20. The beamformer of claim 4, wherein the single crystal piezoelectric substrate is a PMN-PT single crystal piezoelectric substrate.

21. The beamformer of claim 5, wherein the single crystal piezoelectric substrate is a PMN-PT single crystal piezoelectric substrate.

22. The beamformer of claim 6, wherein the single crystal piezoelectric substrate is a PMN-PT single crystal piezoelectric substrate.

23. The beamformer of claim 7, wherein the single crystal piezoelectric substrate is a PMN-PT single crystal piezoelectric substrate.

24. The system of claim 9, wherein each respective variable delay structure is formed of a set of two planar electrodes comprising one planar electrode on each of two opposite surfaces of the substrate.

25. The system of claim 24, wherein the delay control circuit applies a voltage across each respective set of planar electrodes to control the length of each respective variable delay structure.

26. The system of claim 9, wherein each respective variable delay structure is formed of a photoconductive layer on a surface of the respective SAW device.

27. The system of claim 9, further comprising an adder to add the output signals of each SAW device of the linear array.

28. The system of claim 9, wherein the ultrasound output electrode structure of all SAW devices in the linear array is formed as a single electrode pair to sum the variably delayed signals received from the input electrode structures of all SAW devices in the linear array.

29. The system of claim 9, wherein the input and output electrode structures are interdigital electrode structures.

30. The system of claim 9, wherein the single crystal piezoelectric substrate is a PMN-PT single crystal piezoelectric substrate.

31. The probe of claim 10, wherein each respective variable delay structure is formed of a set of two planar electrodes comprising one planar electrode on each of two opposite surfaces of the substrate.

32. The probe of claim 31, wherein the delay control circuit applies a voltage across each respective set of planar electrodes to control the length of each respective variable delay structure.

33. The probe of claim 10, wherein each respective variable delay structure is formed of a photoconductive layer on a surface of the respective SAW device.

34. The probe of claim 10, further comprising an adder to add the output signals of each SAW device of the linear array.

35. The probe of claim 10, wherein the ultrasound output electrode structure of all SAW devices in the linear array is formed as a single electrode pair to sum the variably delayed signals received from the input electrode structures of all SAW devices in the linear array.

36. The probe of claim 10, wherein the input and output electrode structures are interdigital electrode structures.

37. The probe of claim 10, wherein the single crystal piezoelectric substrate is a PMN-PT single crystal piezoelectric substrate.

* * * * *

UNITED STATES PATENT AND TRADEMARK OFFICE
CERTIFICATE OF CORRECTION

PATENT NO. : 10,181,317 B2  
APPLICATION NO. : 13/146620  
DATED : January 15, 2019  
INVENTOR(S) : Jeremy Brown et al.

Page 1 of 1

It is certified that error appears in the above-identified patent and that said Letters Patent is hereby corrected as shown below:

On the Title Page

Item (*), "This patent is subject to a terminal disclaimer" should be deleted.

Signed and Sealed this
Fifth Day of March, 2019

Andrei Iancu
*Director of the United States Patent and Trademark Office*